United States Patent
Pathirana (10) Patent No.: US 10,159,916 B2
(45) Date of Patent: Dec. 25, 2018

(54) SYRINGE FILTER

(71) Applicant: GE Healthcare UK Limited, Buckinghamshire (GB)

(72) Inventor: Navin Deepal Pathirana, Marlborough, MA (US)

(73) Assignee: GE Healthcare UK Limited, Little Chalfont (GB)

( * ) Notice: Subject to any disclaimer, the term of this patent is extended or adjusted under 35 U.S.C. 154(b) by 159 days.

(21) Appl. No.: 15/101,989

(22) PCT Filed: Nov. 26, 2014

(86) PCT No.: PCT/EP2014/075703
§ 371 (c)(1),
(2) Date: Jun. 6, 2016

(87) PCT Pub. No.: WO2015/090877
PCT Pub. Date: Jun. 25, 2015

(65) Prior Publication Data
US 2016/0310874 A1    Oct. 27, 2016

Related U.S. Application Data (60) Provisional application No. 61/917,374, filed on Dec. 18, 2013.

(51) Int. Cl.
*B01D 29/01*     (2006.01)
*B01D 63/08*     (2006.01)
(Continued)

(52) U.S. Cl.
CPC ........... *B01D 29/01* (2013.01); *A61M 1/0068* (2014.02); *A61M 3/0262* (2013.01);
(Continued)

(58) Field of Classification Search
CPC .......................... A61M 1/0068; A61M 5/3145
See application file for complete search history.

(56) References Cited

U.S. PATENT DOCUMENTS 3,747,812 A * 7/1973 Karman ............. A61B 5/15003
222/387
4,137,917 A * 2/1979 Cohen ................. A61M 5/3145
604/190

(Continued)

FOREIGN PATENT DOCUMENTS

WO    9617550 A1    6/1996

OTHER PUBLICATIONS

International Search Report and Written Opinion regarding International Application No. PCT/EP2014/075703, dated Mar. 2, 2015, 9 pages.

*Primary Examiner* — Bobby Ramdhanie
*Assistant Examiner* — Michael J An
(74) *Attorney, Agent, or Firm* — Eversheds Sutherland (US) LLP (57) ABSTRACT

The present invention provides a syringe for filtering a liquid comprising: a housing with a plunger slidable therein; an inlet for taking in liquid from a liquid source into the housing; an outlet for expelling liquid from the inside of the housing; a filter; and a rotatable valve member being rotatable between a first position and a second position; wherein rotation of the valve member to the first position permits liquid that is drawn through the inlet into the housing by pulling the plunger to bypass the filter, and rotation of the valve member to the second position forces liquid that is expelled from the inside of the housing by pushing the plunger to pass through the filter and out of the outlet.

18 Claims, 6 Drawing Sheets

(51) Int. Cl.
*B01L 3/00* (2006.01)
*B01L 3/02* (2006.01)
*A61M 1/00* (2006.01)
*A61M 5/31* (2006.01)
*A61M 3/02* (2006.01)

(52) U.S. Cl.
CPC ........ *A61M 5/3134* (2013.01); *A61M 5/3145* (2013.01); *B01D 63/087* (2013.01); *B01L 3/0206* (2013.01); *B01L 3/50* (2013.01); *B01L 3/502* (2013.01); *A61M 2005/3114* (2013.01); *A61M 2005/3128* (2013.01); *A61M 2205/75* (2013.01); *B01D 2201/204* (2013.01); *B01D 2313/24* (2013.01); *B01L 2200/025* (2013.01); *B01L 2200/0631* (2013.01); *B01L 2300/0681* (2013.01); *B01L 2300/0803* (2013.01); *B01L 2400/0478* (2013.01); *B01L 2400/0644* (2013.01)

(56) References Cited

U.S. PATENT DOCUMENTS

| | | | |
|---|---|---|---|
| 4,253,501 A | | 3/1981 | Ogle |
| 4,784,637 A | * | 11/1988 | Ryder ................. A61M 1/0062 604/236 |
| 4,820,276 A | * | 4/1989 | Moreno ............. A61M 5/3145 222/189.06 |
| 2006/0097013 A1 | | 5/2006 | Bargh |
| 2013/0056403 A1 | | 3/2013 | Collins et al. |

* cited by examiner

SYRINGE FILTER

CROSS-REFERENCE TO RELATED APPLICATIONS

This application is a filing under 35 U.S.C. 371 of international application number PCT/EP2014/075703, filed Nov. 26, 2014, which claims priority to U.S. application No. 61/917,374, filed Dec. 18, 2013, the entire disclosures of each of which are hereby incorporated by reference.

FIELD OF THE INVENTION

The present invention relates to filtration devices and methods of using such devices to filter solutions.

BACKGROUND TO THE INVENTION

Filtration is a common method of separating larger particles in solution from smaller ones. Filters, filtrations devices and filtration methods are used in a wide range of biological and chemical applications for the separation or purification of various moieties.

Syringe filters are used in the art to filter liquids. Such filters are regularly used for the lab-scale filtration of liquids. The use of such filters typically comprises drawing the sample to be filtered into a syringe. The syringe is then attached to a syringe filter and the liquid is then pushed through the filter. Since the syringe and the filter are separate components that are brought together by the end user, filter manufactures cannot control the quality of the syringes that customers use. In some circumstances, use of the wrong syringe can result in leachables from the syringe entering the filtrate.

Often, when extracting a sample that requires filtration it is necessary to filter a volume of liquid larger than the volume of the syringe. In such circumstances, once the user has pushed the liquid from the syringe through the filter, the user would then have to remove the filter in order to draw up more of the (unfiltered) liquid sample into the syringe. The filter would then need to be replaced for the dispensing stage to ensure that the sample liquid is filtered. This process would need to be repeated until the full volume of liquid sample has been filtered. This can be time consuming and burdensome for the user. Furthermore, the need to move the syringe between filtration steps and to remove and re-attach the filter increases the risk of contamination of the solution to be filtered.

It would be desirable to provide a filtration device that permits the user to draw in and filter a solution without having to change or remove the filter to refill the syringe. GE Healthcare have commercialised a filtration device, a Clyde in-line filter, through its Whatman™ portfolio. The Clyde™ device is a single device system comprising a sample inlet pipe, a one-way valve, a flat filter, a syringe and connecting pipework. The device permits a user to filter up to 2 L of solution in a continuous process. The device can be built with a limited number of available filters.

However, there is a continuing need in the art to provide alternative forms of "one way" filters that can be manufactured on a large scale from readily available, cost-effective materials and which are simple and easy to operate by a user—typically a lab researcher or technician.

SUMMARY OF THE INVENTION

According to a first aspect of the present invention, there is provided a syringe for filtering a liquid comprising:

a housing with a plunger slidable therein; an inlet for taking in liquid from a liquid source into the housing; an outlet for expelling liquid from the inside of the housing; a filter; and a rotatable valve member being rotatable between a first position and a second position;

wherein rotation of the valve member to the first position permits liquid that is drawn through the inlet into the housing by pulling the plunger to bypass the filter, and rotation of the valve member to the second position forces liquid that is expelled from the inside of the housing by pushing the plunger to pass through the filter and out of the outlet.

In one embodiment, the rotatable valve member is located between the filter and the inlet and outlet.

In a further embodiment, the housing comprises a side wall and opposed spaced apart first and second ends separated at least in part by the side wall, the plunger being inserted through the first end, and the inlet, the outlet, the filter; and the rotatable valve member each being located at the second end.

In a further embodiment, rotation of the valve member to the first position opens a first liquid path between the inlet and the inside of the housing which bypasses the filter; and rotation of the valve member to the second position closes the first liquid path, thereby forcing liquid that is expelled from the housing to pass through a second liquid path between the inside of the housing and the outlet that passes through the filter.

In a further embodiment, the valve member blocks the second liquid path when the valve member is in the first position. In a further embodiment, rotation of the valve member to the second position opens the second liquid path.

In a further embodiment, the valve member comprises a first aperture which aligns with the inlet to open the first liquid path when the valve member is in the first position. In a further aspect of this embodiment, the valve member comprises a second aperture that aligns with the outlet to open the second liquid path when the valve member is in the second position, and wherein the first and second apertures are spaced apart on the valve member such that the first aperture cannot align with the inlet when the second aperture is aligned with the outlet and vice-versa.

In a further embodiment, the valve member comprises a rotatable disc. In a further embodiment, the valve member is rotatable about an axis that is substantially parallel to the length of the housing.

In a further embodiment, the filter is substantially circular in shape. The filter is preferably a membrane filter.

In a further embodiment, the valve member comprises a lever to facilitate rotation of the valve member between the first position and the second position.

In a further embodiment, the inlet and the outlet are formed by conduits extending from the base of the housing. In a further aspect of this embodiment, the inlet conduit extends further than the outlet conduit and/or the inlet conduit has a larger internal bore than the outlet conduit.

In a preferred embodiment, the filter is fixed to the housing of the syringe.

In a preferred embodiment, the housing and the rotatable valve member are made of plastic.

In a second aspect of the present invention, there is provided a method of filtering a liquid comprising (a) providing a syringe according to the present invention;
(b) checking that the valve member is in the first position and, if necessary rotating the valve member to the first position;

(c) pulling the syringe plunger to draw liquid from the liquid that is to be filtered into the housing of the syringe;

(d) rotating the valve member to the second position; and (e) pushing the syringe plunger to filter liquid through the filter and expel the liquid through the outlet.

By providing a syringe as described above, a user can, by hand, draw sample from a bulk solution and dispense the drawn sample through the filter in a continuous fashion without the need to remove the filter in the event that the housing cannot accommodate the full volume of liquid that is to be filtered. Furthermore, the provision of an all-in-one device that can both draw in liquid and then filter the liquid permits manufactures to ensure that end-users use the appropriate combination of syringe and filter to optimise output quality. The syringe according to the present invention also provides a low cost component to a filtering application within the laboratory.

DETAILED DESCRIPTION OF THE INVENTION

According to a first aspect of the present invention, there is provided a syringe for filtering a liquid comprising: a housing with a plunger slidable therein; an inlet for taking in liquid from a liquid source into the housing; an outlet for expelling liquid from the inside of the housing; a filter; and a rotatable valve member being rotatable between a first position and a second position; wherein rotation of the valve member to the first position permits liquid that is drawn through the inlet into the housing by pulling the plunger to bypass the filter, and rotation of the valve member to the second position forces liquid that is expelled from the inside of the housing by pushing the plunger to pass through the filter and out of the outlet.

Figure 1:
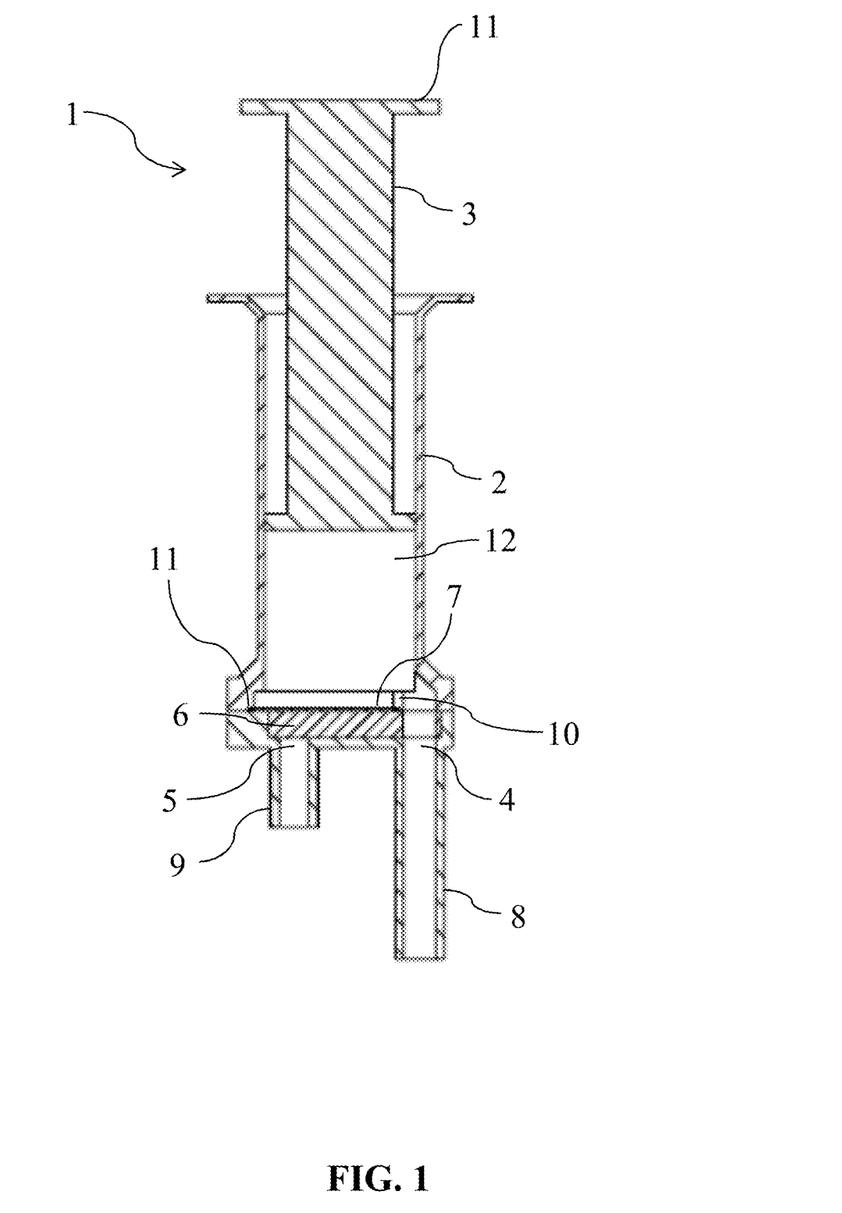
FIG. 1 is a sectional view of a syringe according to the present invention.
Figure 2A:
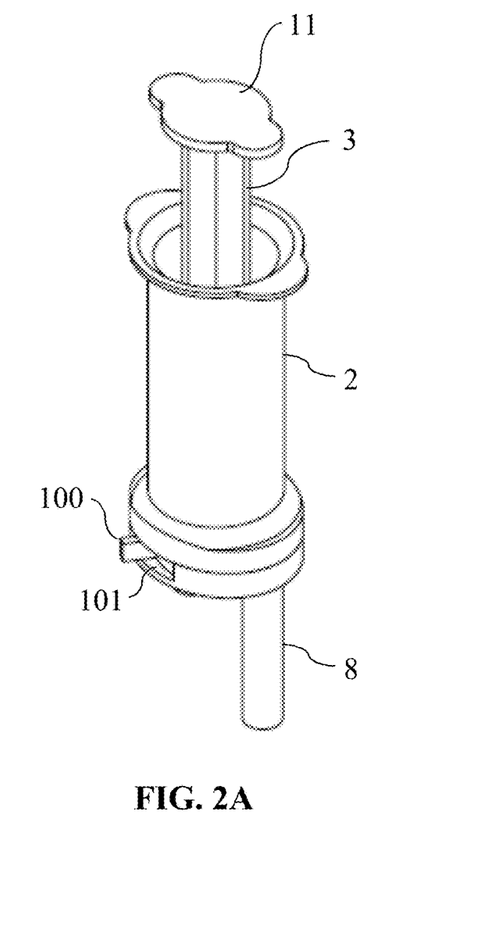
FIG. 2A is a three dimensional schematic of a syringe according to the present invention.
Figure 2B:
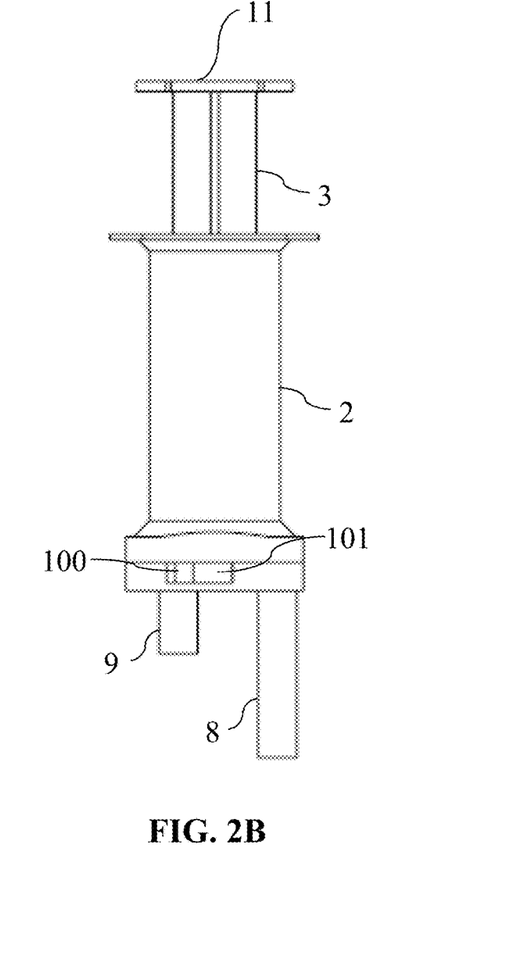
FIG. 2B is a front view of the syringe shown in FIG. 2A.
Figure 2C:
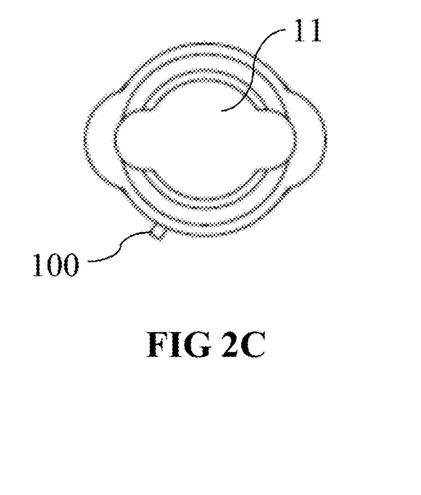
FIG. 2C is plan view of the syringe shown in FIG. 2A when view from above the syringe.
Figure 2D:
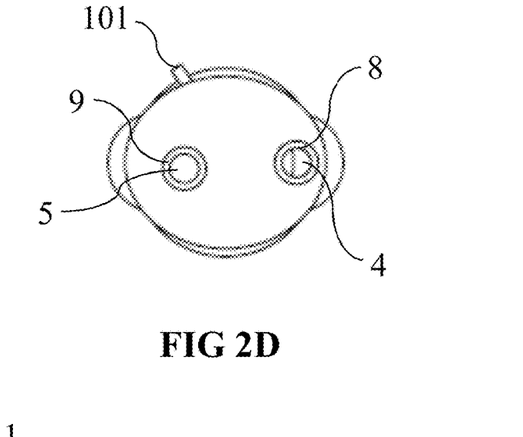
FIG. 2D is a plan view of the syringe shown in FIG. 2A when viewed from below the syringe.
Figure 2E:
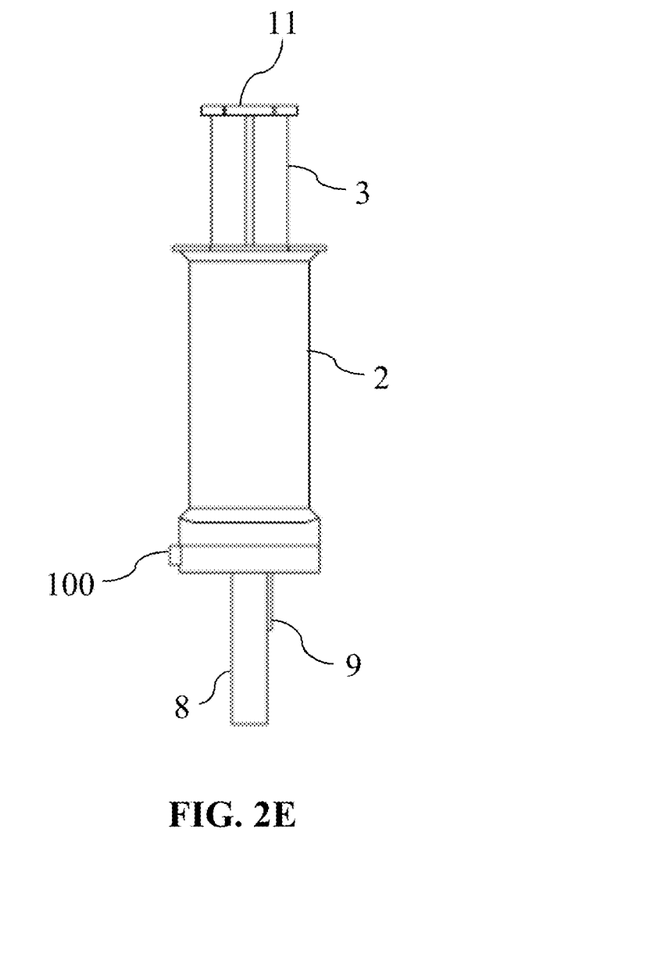
FIG. 2E is a side view of the syringe shown in FIG. 2A.

FIG. 1A is a sectional view of a syringe according to the present invention. The syringe 1 comprises a plunger 3, the plunger being slidable within a syringe housing 2 via the plunger handle 11. The syringe comprises an inlet 4 for taking in liquid from a liquid source and an outlet 5 for expelling liquid from the inside of the housing 2. The housing, in combination with the plunger and rotatable valve member 6, will typically provide a water-tight enclosure such that liquid can only enter and exit the housing via the inlet and outlet. Accordingly, the housing and plunger should be constructed from a water impermeable material, for example a plastic such as, but not limited to, polypropylene.

The inlet 4 and outlet 5 are typically formed by conduits such as tubular channels, 8, 9, extending from the base of the housing. The inlet and/or outlet may comprise luer-type and/or tapered fitting connection points to permit easy-to-use, liquid-tight points. The inlet and/or outlet may, for example, be fitted with e.g. pipette tips or the like to facilitate liquid uptake or expulsion. In a preferred embodiment, the inlet conduit or tube 8 extends further than the outlet conduit or tube 9, thereby making it easier to pick up the unfiltered liquid without contaminating the outlet.

The syringe comprises a filter 7 and a rotatable valve member 6. The filter 7 is typically a flat or membrane filter. The filter will separate wanted (or unwanted) particles in the liquid from the remainder of the liquid (the filtrate). Multiple types of filters may be used. In a preferred embodiment, the filter comprises one or more membrane filters. The filter may comprise a filter stack, for example comprising a pre-filter (e.g. a glass microfiber filter(s)) stacked with one or more membrane filters. Suitable materials for the filter include PTFE, polypropylene, RC, PVDF, nylon or glass fibre. Pore sizes typically range from 0.1 µm to 0.7 mm, but can be outside of this window. The thickness of the filter can vary greatly, typically ranging from 0.05 µm to around 0.25 mm. The diameter of the filter may be in the range of 10 mm to 50 mm, preferable 10 mm and 30 mm. The filter element is preferable fixed to the housing of the syringe. This can be achieved for example, by a groove or cavity 11 on the inside of the housing which accommodates and fixes the filter element. An inside wall member 10 may serve to separate the inlet path 4 from the membrane 7.

The rotatable valve member 6 is preferably located beneath the membrane and above the inlet 4 and outlet 5. The valve member is preferably rotatable about an axis that is substantially parallel to the length of the housing e.g. an axis extending from the longitudinal length of the plunger. The rotatable valve member is rotatable by a user between a first position and a second position. The first position permits liquid that is drawn through the inlet 4 in the housing (by pulling the plunger handle 11) to bypass the filter 7. The second position ensures that liquid that is expelled from the inside of the housing (through pushing the plunger handle 11) passes through the filter 7 and out of the outlet 5. By being position between the filter 7 and the inlet and outlet 4, 5, the valve member 7 can be toggled between the first and second positions such that the position of the valve member dictates whether liquid is able to pass through the inlet and outlet. In order to achieve this, the valve member should be made of a water impermeable material, such a suitable plastic. In order to permit the easy rotation of the valve member 6, the valve member may have a lever 100 which the user may grip to toggle between the first and second positions, as shown in FIG. 2. The lever 100 may extend through a window or opening 101 in the side of the housing. The movement of the lever is dictated by the size of the window 101. Accordingly, the size of the window can be used to guide the user between the first and second position. For example, when the user rotates the valve member by pulling the lever until it abuts the edge of the window, the valve member will be positioned in the first or second position. Likewise, when the user rotates the valve member in the opposite direction by pushing the lever to abut the opposed edge of the window, the valve member will then be position in the other of the first or second position.

Figure 3A:
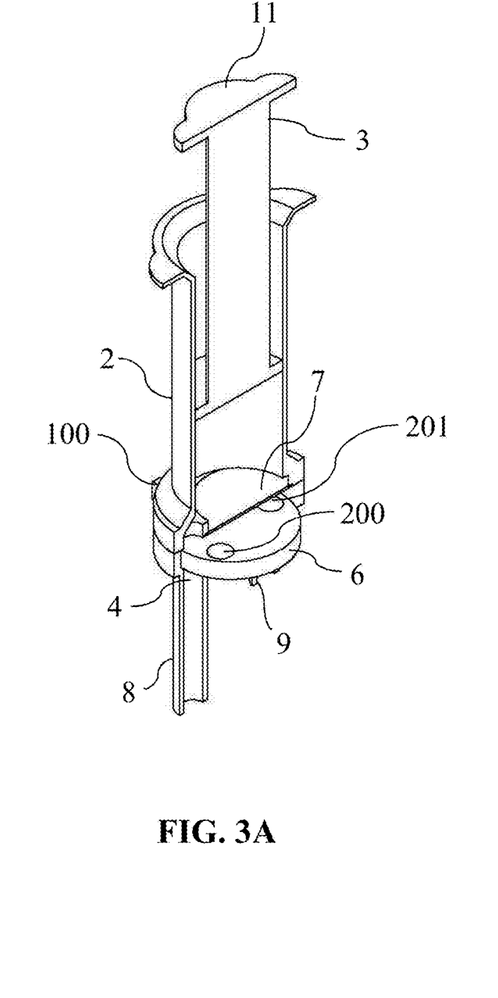
FIG. 3A is a three dimensional transverse sectional view of a syringe according to the present invention showing how the rotatable valve member (shown as a complete three dimension view and not as a sectional view) can be integrated into the syringe.
Figure 3B:
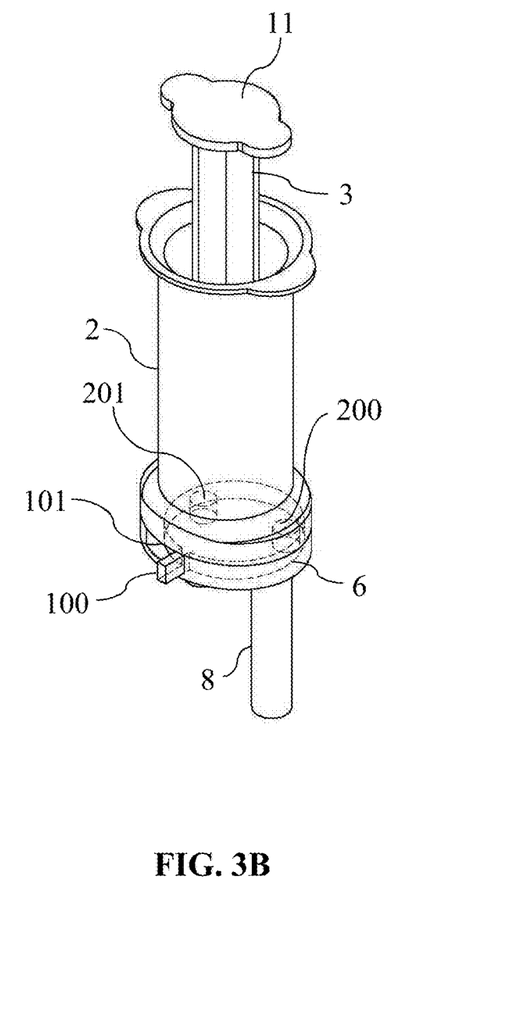
FIG. 3B is a three dimensional schematic of a syringe according to the present invention, with the part of the rotatable valve member that would otherwise be hidden from view being shown by the dotted line.

FIG. 3A is a three dimensional transverse sectional view of a syringe according to the present invention showing how the rotatable valve member can be integrated into the syringe. The valve member is shown, for convenience purposes, as a three dimension view and not as a sectional view. With reference to FIG. 3A, the valve member 6 is preferable in the form of a disc with a first aperture 200 which can be rotated to a first position to align with the inlet 4 to form a first liquid path between the inlet and the inside of the housing which bypasses the filter 7. The valve member 6 further comprises a second aperture 201 that can be rotated to align with the outlet (not shown) to open a second liquid path between the inside of the housing and the outlet that passes through the filter. The first and second apertures preferably each traverse opposed faces of the disc. The term "align" used herein with respect to an aperture and an inlet/outlet should be understood to mean that the aperture and inlet or aperture and outlet overlap sufficiently (e.g. either exactly or partially) in order to create a liquid path.

It is possible for the valve member to have only a single aperture that can be rotated between the inlet 4 and outlet 5. However, the presence of two apertures 200 and 201 is advantageous as this reduces the rotation angle necessary to open the first and second liquid paths. Furthermore, by employing two apertures, the risk of contamination between filtered and unfiltered liquid is reduced.

Figure 4:
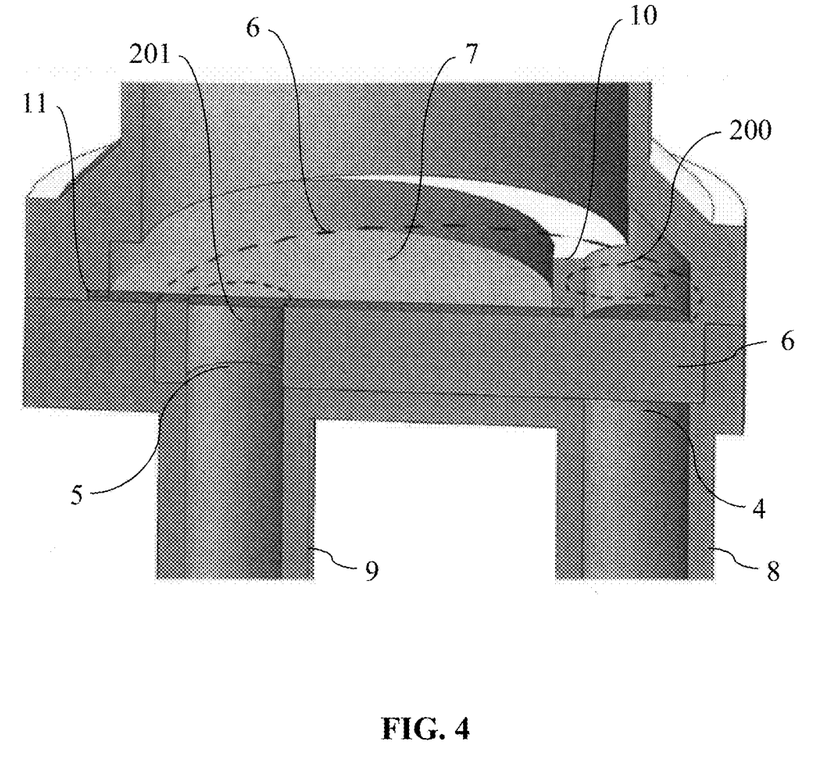
FIG. 4 is a three dimensional transverse sectional view of part of a syringe according to the present invention, with the part of the rotatable valve member that would otherwise be hidden from view being shown by the dotted line.

FIG. 4 is a three dimensional transverse sectional view of part of a syringe according to the present invention, with the part of the rotatable valve member 6 that would otherwise be hidden from view being shown by the dotted line. FIG. 4 shows the valve member 6 positioned such that the aperture 201 is aligned with the outlet 5. When the valve is in this position, the aperture 200 is not aligned with the inlet 4 and so inlet 4 is blocked by the valve member 6. However, rotation of the valve member 6 to position aperture 200 over outlet 4 would have the consequence of simultaneously providing a liquid path through the opening 4 to the inside of the housing and moving aperture 201 away from outlet 5, thereby blocking the liquid path between the inside of the housing and outlet 5.

Figure 5A:
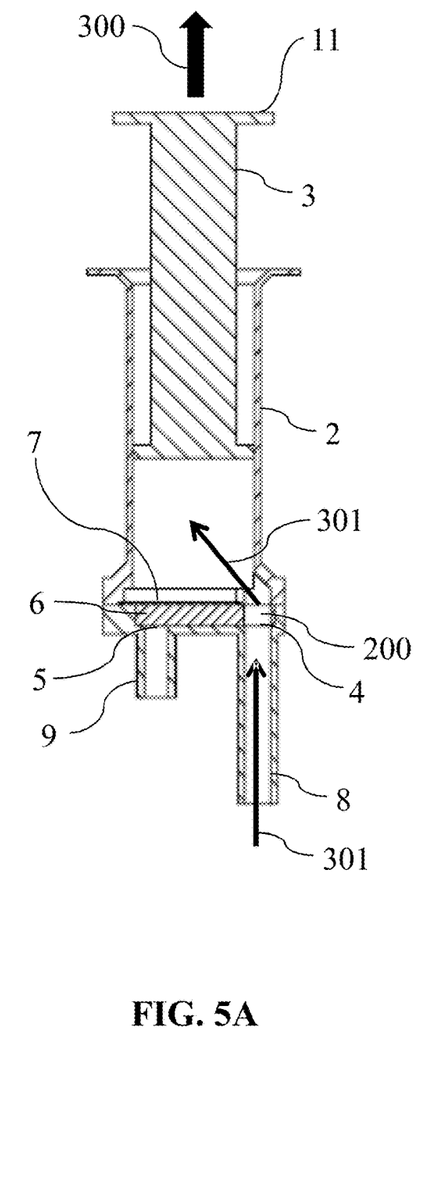
FIG. 5A is a sectional view of a syringe according to the present invention, showing how liquid is drawn into the syringe.

FIG. 5A is a sectional view of a syringe according to the present invention, showing how liquid is drawn into the syringe. The valve member 6 is rotated such that the aperture 200 of the valve member is aligned with the inlet 4 to provide a liquid path between the inlet and the inside of the syringe. In this position, the valve member blocks the inlet 5. Conduit 8 is connected (either directly or e.g. through further tubing or a pipette tip) to the liquid that is to be filtered. The handle 11 of the plunger 3 is pulled upwards (as shown by arrow 300), thereby drawing liquid into the syringe via aperture 200 as shown by the arrows 301. In this way, liquid is drawn into the syringe via a liquid path that bypasses the filter.

Figure 5B:
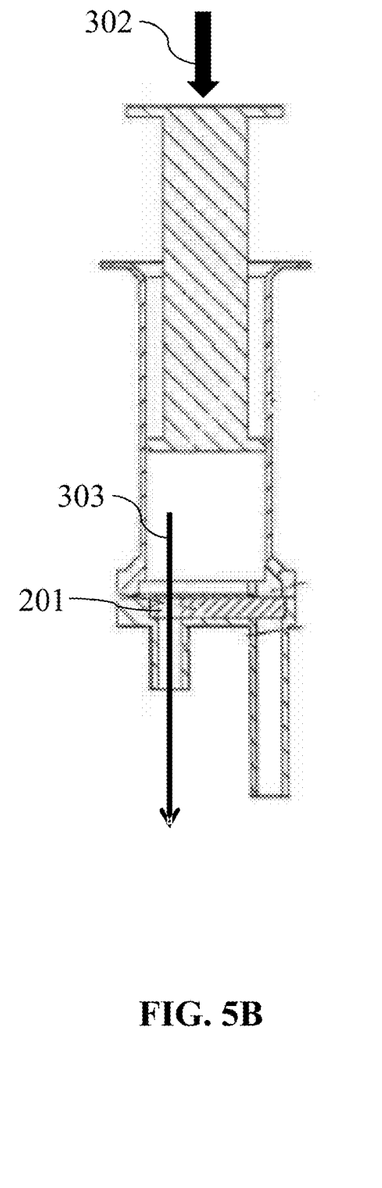
FIG. 5B is a sectional view of a syringe according to the present invention, showing how liquid is expelled from the syringe.

FIG. 5B is a sectional view of a syringe according to the present invention, showing how liquid that has been drawn into the syringe (as shown in FIG. 5A) is subsequently expelled from the syringe. The valve member is rotated such that aperture 201 aligns with the outlet 5 and the liquid path between the inlet and the inside of the syringe is closed. The handle of the plunger is pushed, thereby forcing liquid from the inside of the syringe through the filter and out, via aperture 201, through the outlet. Since the liquid path between the inlet and the syringe is closed, the only way liquid can pass through the syringe is through the filter. Accordingly, liquid that is pushed from the syringe is filtered.

The invention claimed is:

1. A syringe for filtering a liquid comprising:
a housing with a plunger slidable therein; an inlet for taking in liquid from a liquid source into the housing; an outlet for expelling liquid from the inside of the housing; a filter; and a rotatable valve member being rotatable between a first position and a second position; wherein the valve member comprises a lever to facilitate rotation of the valve member between the first position and the second position;
wherein rotation of the valve member to the first position permits liquid that is drawn through the inlet into the housing by pulling the plunger to bypass the filter, and rotation of the valve member to the second position forces liquid that is expelled from the inside of the housing by pushing the plunger to pass through the filter and out of the outlet.

2. A syringe according to claim 1, wherein the rotatable valve member is located between the filter and the inlet and outlet.

3. A syringe according to claim 2, wherein rotation of the valve member to the first position opens a first liquid path between the inlet and the inside of the housing which bypasses the filter; and rotation of the valve member to the second position closes the first liquid path, thereby forcing liquid that is expelled from the housing to pass through a second liquid path between the inside of the housing and the outlet that passes through the filter.

4. A syringe according to claim 3, wherein the valve member blocks the second liquid path when the valve member is in the first position.

5. A syringe according to claim 4, wherein rotation of the valve member to the second position opens the second liquid path.

6. A syringe according to claim 5, wherein the valve member comprises a first aperture which aligns with the inlet to open the first liquid path when the valve member is in the first position.

7. A syringe according to claim 6, wherein the valve member comprises a second aperture that aligns with the outlet to open the second liquid path when the valve member is in the second position, and wherein the first and second apertures are spaced apart on the valve member such that the first aperture cannot align with the inlet when the second aperture is aligned with the outlet and vice-versa.

8. A syringe according to claim 7, wherein the valve member comprises a rotatable disc.

9. A syringe according to claim 8, wherein the valve member is rotatable about an axis that is substantially parallel to the length of the housing.

10. A syringe according to claim 9, wherein the filter is substantially circular in shape.

11. A syringe according to claim 10, wherein the filter comprises a membrane filter.

12. A syringe according to claim 11, wherein the inlet and the outlet are formed by conduits extending from the base of the housings.

13. A syringe according to claim 12, wherein the inlet conduit extends further than the outlet conduit.

14. A syringe according to claim 13, wherein the inlet conduit has a larger internal bore than the outlet conduit.

15. A syringe according to claim 14, wherein the filter is fixed to the housing of the syringe.

16. A syringe according to claim 15, wherein the housing and the rotatable valve member are made of plastic.

17. A method of filtering a liquid comprising
  (a) providing a syringe;
  (b) checking that the valve member comprising a lever to facilitate rotation of the valve member between the first position and the second position is in the first position and, if necessary rotating the valve member to the first position;
  (c) pulling the syringe plunger to draw liquid from the liquid that is to be filtered into the housing of the syringe;
  (d) rotating the valve member to the second position; and
  (e) pushing the syringe plunger to filter liquid through the filter and expel the liquid through the outlet.

18. A method of filtering a liquid, comprising: filtering the liquid with the syringe of claim 1.

* * * * *